United States Patent
Clavel

(10) Patent No.: US 11,583,359 B2
(45) Date of Patent: Feb. 21, 2023

(54) DOUBLE PACKAGING FOR OBJECT INTENDED TO REMAIN STERILE

(71) Applicant: A. RAYMOND ET CIE, Grenoble (FR)

(72) Inventor: Maxime Clavel, Vif (FR)

(73) Assignee: A. RAYMOND ET CIE, Grenoble (FR)

(*) Notice: Subject to any disclaimer, the term of this patent is extended or adjusted under 35 U.S.C. 154(b) by 129 days.

(21) Appl. No.: 16/919,796

(22) Filed: Jul. 2, 2020

(65) Prior Publication Data
US 2021/0000559 A1    Jan. 7, 2021

(51) Int. Cl.
| | |
|---|---|
| *B65D 83/10* | (2006.01) |
| *A61B 50/30* | (2016.01) |
| *A61C 8/00* | (2006.01) |
| *A61B 50/00* | (2016.01) |

(52) U.S. Cl.
CPC .......... *A61B 50/30* (2016.02); *A61C 8/0087* (2013.01); *A61B 2050/0082* (2016.02); *A61B 2050/3006* (2016.02); *A61C 2201/00* (2013.01); *A61C 2202/00* (2013.01)

(58) Field of Classification Search
CPC .. B65D 83/005; B65D 85/1009; A61B 50/30; A61B 2050/0082; A61B 2050/3006
USPC ....... 206/305, 306, 363, 63.5, 368, 438, 804
See application file for complete search history.

(56) References Cited

U.S. PATENT DOCUMENTS

| | | | | |
|---|---|---|---|---|
| 3,070,224 A * | 12/1962 | Robinson | ............ | B65D 83/005 206/525 |
| 3,403,714 A * | 10/1968 | Hulmjohn | ............ | B65D 50/065 206/815 |
| 4,293,359 A * | 10/1981 | Jakobsen | ................ | B29C 65/02 215/10 |
| 5,607,050 A * | 3/1997 | Dolan | .................. | A61C 15/043 206/408 |
| 5,622,500 A * | 4/1997 | Niznick | ............... | A61C 8/0048 206/63.5 |
| 6,428,310 B1 * | 8/2002 | Nicholas G. | ............ | C11C 5/023 249/94 |

(Continued)

FOREIGN PATENT DOCUMENTS

| | | |
|---|---|---|
| WO | 01/92117 A2 | 12/2001 |
| WO | 2012/172215 A2 | 12/2012 |

OTHER PUBLICATIONS

European Search Report and Search Opinion Received for EP Application No. 20179650, dated on Nov. 27, 2020, 5 pages.

*Primary Examiner* — Luan K Bui
(74) *Attorney, Agent, or Firm* — TraskBritt

(57) ABSTRACT

A double packaging structure for an object, which may be a sterile object, includes a hollow external container having a closed first end, an open second end and walls, and an internal container disposed inside the external container. The internal container includes a hollow body and a cap. The object is intended to be received in the body. To close its first end, the external container has a membrane capable of deforming when pressure is applied to the membrane. The membrane is configured so that a pressure applied to its outer face, along the longitudinal axis, pushes its inner face against the inner container and causes the inner container to exit at the second end of the external container in the absence of a closure system at the second end.

19 Claims, 4 Drawing Sheets

(56) References Cited

U.S. PATENT DOCUMENTS

| | | | |
|---|---|---|---|
| 2010/0038273 A1* | 2/2010 | Johnson | B01L 3/508 |
| | | | 53/473 |
| 2017/0369198 A1* | 12/2017 | Levy | B65B 3/04 |
| 2018/0178963 A1 | 6/2018 | Richart | |
| 2019/0175275 A9 | 6/2019 | Richart | |

* cited by examiner

DOUBLE PACKAGING FOR OBJECT INTENDED TO REMAIN STERILE

PRIORITY CLAIM

This application claims the benefit of the filing date of French Patent Application Serial No. FR1907412, filed Jul. 3, 2019, for "Double Packaging for Object Intended to Remain Sterile," the disclosure of which is incorporated herein by this reference.

TECHNICAL FIELD

The present disclosure relates to the field of packaging that is particularly suitable for objects intended to remain sterile until use or implantation. More particularly, the present disclosure relates to double packaging for an implant type object, such as a dental or orthopedic implant.

BACKGROUND

The state of the art of the packaging is presented in the form of an external and internal double envelope of the bag or double shell type, containing an object, in particular a sterilized medical product. From its departure from a non-sterile zone (storage zone) to its arrival in a sterile zone (for example an operating room), the packaging is contaminated at the level of its outer envelope. It is therefore important to avoid any risk of contamination by direct or indirect contact between this outer envelope and the inner envelope or even the product itself.

For this, it is known that a first operator opens the outer envelope, in a sterile zone, and drops the inner envelope on a work surface; a second operator then opens the inner envelope to remove the sterilized object. The disadvantage of this approach is that the inner envelope, and therefore the object it contains, are liable to fall to the ground accidentally, and thus to be impacted by shock and contaminated by foreign bodies present on the ground.

According to another approach, the first operator can open the external envelope and hold it so that the second operator grasps the internal envelope, taking care not to touch the external envelope. This is the approach proposed for example in International Patent Application Publication No. WO2012/172215.

BRIEF SUMMARY

The present disclosure provides an alternative to the approaches of the prior art. The present disclosure relates to a double packaging for an object, for example an orthopedic or dental implant, intended to remain sterile until use, the double packaging allowing both keeping in the external container of the internal container accommodating the object, and extracting the simple internal container and meeting the sterility requirements.

A double packaging for an object preferably intended to remain sterile until use comprises:
- a hollow external container extending generally along a longitudinal axis and comprising a first closed end, a second open end and walls connecting the first and the second end, the second end being intended to be closed by a closure system,
- an internal container, placed inside the external container, comprising a hollow body and a cap, the object being intended to be received in the body.

The double packaging is notable in that:
- the external container comprises, to close its first end, a membrane capable of deforming when pressure is applied to the membrane,
- the membrane has an outer face and an inner face and is configured so that a pressure applied to its outer face, along the longitudinal axis, pushes its inner face against the internal container and causes the latter to exit at the level of the second end of the external container, in the absence of the closure system.

According to other advantageous and non-limiting characteristics of the present disclosure, taken alone or in any technically feasible combination:
- the walls of the external container define a tubular shape, the central axis of which is the longitudinal axis and having a square, rectangular, polygonal, circular or elliptical section;
- the walls of the outer container include at least a first rib on an inner surface, the first rib being adapted to keep the inner container stuck in the outer container, when no pressure is applied to the membrane;
- the (at least one) first rib is positioned on the side of the first end of the external container, or even near the first end;
- the membrane is liable to deform elastically when pressure is applied to the membrane;
- the outer face of the membrane has a convex shape, when no pressure is applied to the membrane;
- the membrane has a generally hemispherical or semi-ellipsoid shape;
- the inner face of the membrane has at least a second rib, adapted to keep the internal container stuck in the external container, when no pressure is applied to the membrane;
- the cap of the internal container is provided with an object holder, intended to fix the object inside the body;
- the object holder is formed from a flexible or rigid plastic material, and has a generally tubular shape defining a housing in which the object is held;
- the walls of the outer container and the body of the inner container are formed from a rigid plastic material, such as acrylonitrile butadiene styrene (ABS), polycarbonate (PC), a mixture of acrylonitrile butadiene styrene and polycarbonate (ABS-PC), polyesters or co-polyesters, or polypropylene (PP);
- the cap of the internal container is formed from a flexible plastic material, chosen from thermoplastic elastomers (TPE), polystyrene-b-polyethylene-butylene-b-polystyrene (SEBS) and silicone, or from a rigid plastic material such as acrylonitrile butadiene styrene (ABS), polycarbonate (PC), a mixture of acrylonitrile butadiene styrene and polycarbonate (ABS-PC), polyesters or co-polyesters, or polypropylene (PP);
- the membrane of the outer container is formed from a material chosen from thermoplastic elastomers (TPE), polystyrene-b-polyethylene-butylene-b-polystyrene (SEBS) and silicone;
- the membrane is fixed to the walls of the external container by overmolding or by bi-injection;
- the double packaging comprises the closure system, the closure system being formed by a cover fixed to the walls of the external container, at the second end, by sealing, by heat-welding or by bonding; and/or
- the cover is waterproof or porous.

BRIEF DESCRIPTION OF THE DRAWINGS

Other characteristics and advantages of the present disclosure will emerge from the detailed description of certain embodiments of the present disclosure, which follows with reference to the appended figures in which.

The figures are schematic representations which, for the sake of readability, are not necessarily to scale.

DETAILED DESCRIPTION

The present disclosure relates to a double packaging 100 for an object 1 (visible in the sectional view of FIG. 2B) preferably intended to remain sterile until use. Object 1 could, for example, be a medical device, such as an orthopedic or dental implant.

Figure 1:
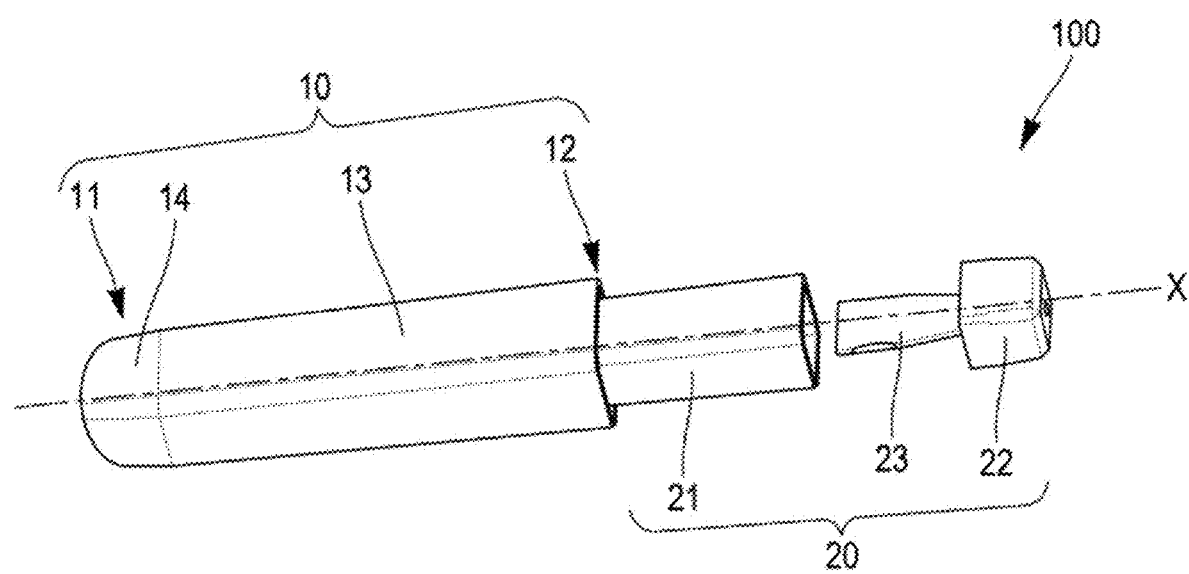
FIG. 1 shows a perspective view of a double package according to the present disclosure.

As illustrated in FIG. 1, the double packaging 100 comprises a hollow external container 10 extending generally along a longitudinal axis X. The external container 10 comprises a first closed end 11, a second open end 12 and walls 13 connecting the first 11 and the second 12 end. The second end 12 is intended to be sealed in a sealed manner by a closure system (not shown).

Figure 2A:
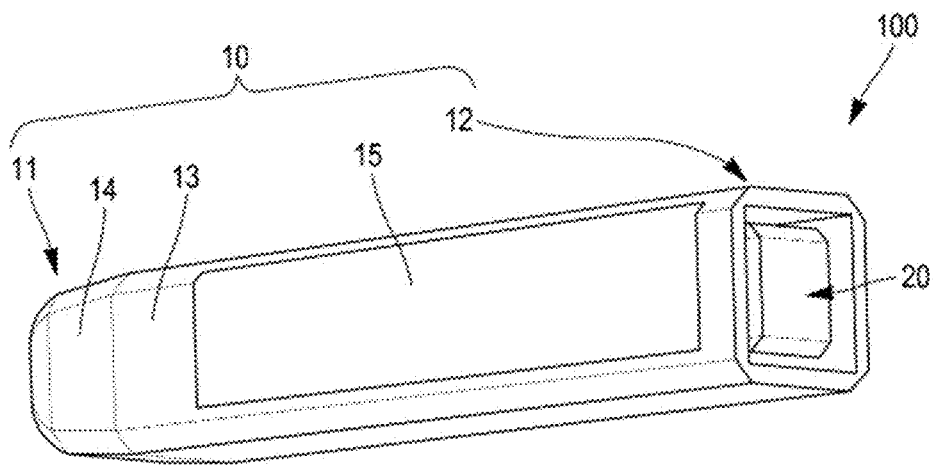
FIGS. 2A and 2B, respectively, show a perspective view and a sectional view of a double packaging, according to the present disclosure.
Figure 4:
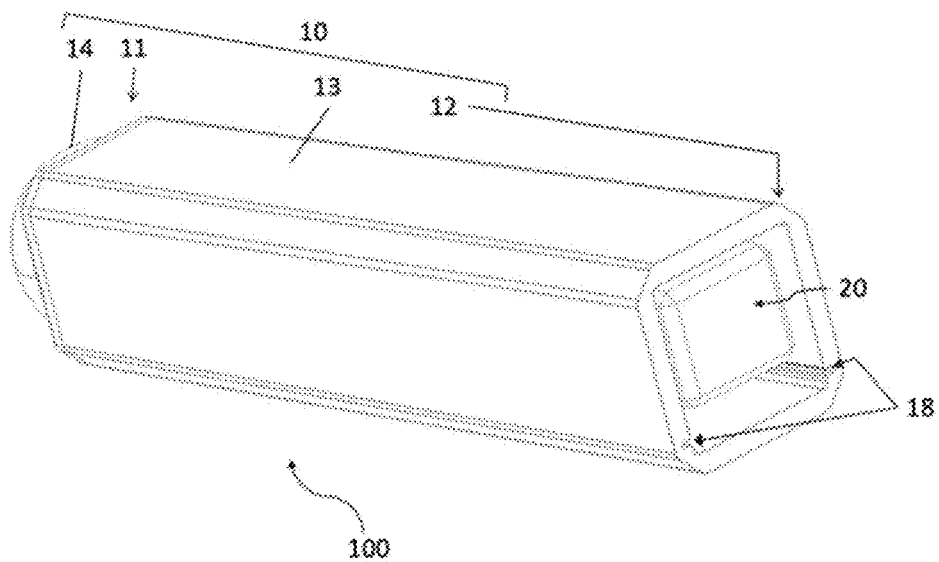
FIG. 4 shows a perspective view of a double packaging according to the present disclosure.

The walls 13 of the external container 10 define a tubular shape, the central axis of which is the longitudinal axis X. The cross-section of the external container 10 can be of any shape, for example square, rectangular, polygonal, circular or elliptical. In the examples illustrated, the section of the external container 10 is substantially square and has rounded edges at its external surface, as can be seen in FIGS. 2A and 4. These rounded edges make the external container 10 more ergonomic and, in particular, facilitate the fitting of labels on the walls 13 of the external container 10, in particular at the location 15 (FIG. 2A).

An alternative to the placement of labels on an outside face of the walls 13 of the external container 10 is the arrangement of notches 18 inside the walls 13, as illustrated in FIG. 4, adapted to accommodate a label or a small booklet. These notches 18 form a slide into which the label or the label holder is introduced. This alternative is advantageous in that it avoids any loss or damage to the label during storage of the double packaging 100 and keeps the label in a sterile medium until use.

To close its first end 11, the external container 10 includes a membrane 14 capable of deforming when pressure is applied to it. The membrane 14 is formed from a flexible and deformable material. Advantageously, it is able to undergo elastic deformation under the effect of pressure and to regain its initial shape when the pressure is no longer applied. The membrane 14 could alternatively be formed from a material capable of deforming plastically when pressure is applied to it, without recovering its initial shape, thus excluding any subsequent reuse.

The membrane 14 has an outer face 14a and an inner face 14b. The shape of this membrane 14 and to the preferred materials from which it may be made are described in further detail subsequently herein.

The double packaging 100 also comprises an internal container 20, which comprises a hollow body 21 and a cap 22, the object 1 being intended to be received in the body 21. Preferably, the cap 22 is forcibly mounted at the open end of the body 21. Alternatively, it could be screwed, clipped or be in the form of a seal sealed at the end of the body 21.

The shape and dimensions of the internal container 20 are adapted so that it can be placed inside the external container 10, without excessive friction against the internal surface of the walls 13.

Figure 2B:
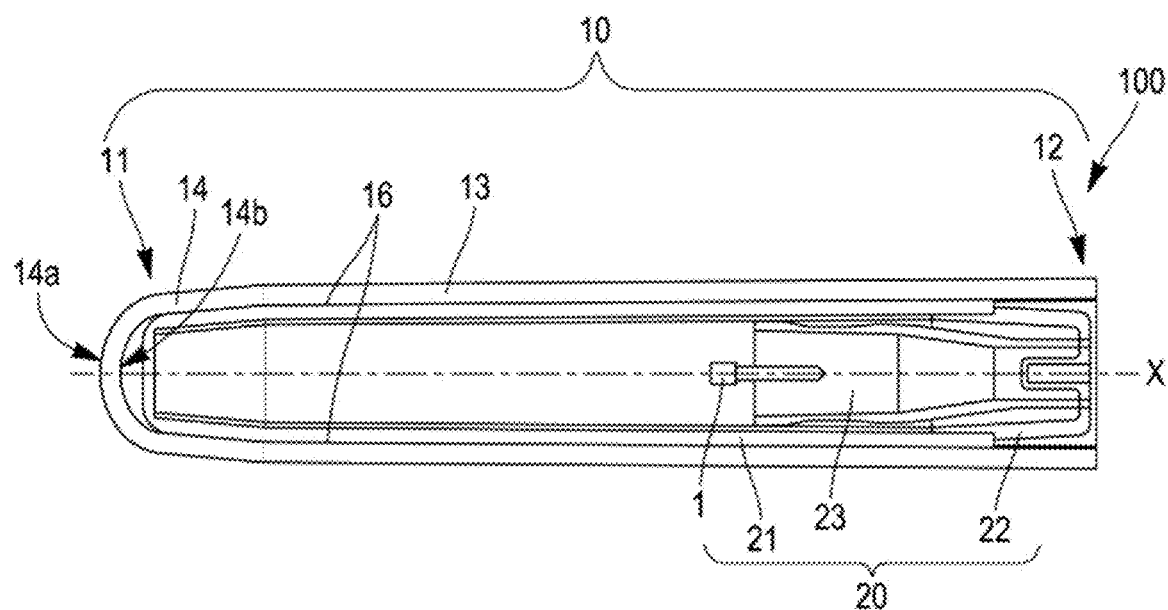

When it is placed in the external container 10, the internal container 20 is completely included therein and does not protrude at the second end 12 (FIGS. 2a and 2b). It is thus understood that the closure system can be placed at the second end 12, against the walls 13 of the external container 10, to close the latter and form a closed and sealed double packaging 100, capable of containing the sterile object 1 until the closure system is removed at the time of use.

According to an advantageous embodiment, the closure system is formed by a cover fixed to the walls 13 of the external container 10, at the level of the second end 12. Different fixing methods may be used, including in particular a sealing, heat-sealing or bonding method. The cover can be formed from different materials, such as for example from aluminum, plastic, multi-complex materials or TYVEK®, synthetic non-woven fabric comprising polyethylene fibers.

According to another embodiment, the closure system is formed by a screwed, clipped or force-fitted plug.

The material(s) which form(s) the closure system may be chosen to be waterproof or porous, depending on the employed sterilization process.

In fact, when the object 1 is placed in the internal container 20, which is inserted in the external container 10, and the closure system is in place on the walls 13, the double packaging 100 can undergo a sterilization step, for example by exposure to gamma rays. Gamma rays pass through the two containers 10, 20 and kill any potentially present bacteria, viruses or other living cells present in the external container 10, in the internal container 20, on and possibly in or on the object 1. After this sterilization step, the double packaging 100 can be stored until it is used in a sterile operating room, for example. With this sterilization process, the closure system is advantageously chosen to be sealed.

Alternatively, sterilization with ethylene oxide (EtO) or autoclave sterilization can be applied to the double packaging 100 provided with the closure system. In this case, the material of the system is chosen to be porous, so as to allow the passage of gas or water vapors, but not the passage of liquids or other contaminants. The cap 22 of the internal container 20 is also chosen to be porous (for example, in the form of a seal sealed to the body 21). For example, the closure system of the external container 10 and the cap 22 of the inner container 20 may, in this case, be in the form of lids composed of TYVEK®.

With reference to FIG. 1, the cap 22 of the internal container 20 is provided with an object holder 23, intended to fix the object 1 inside the body 21. The object holder 23 can have different shapes and have different fixing methods to hold the object 1.

Figure 3A:
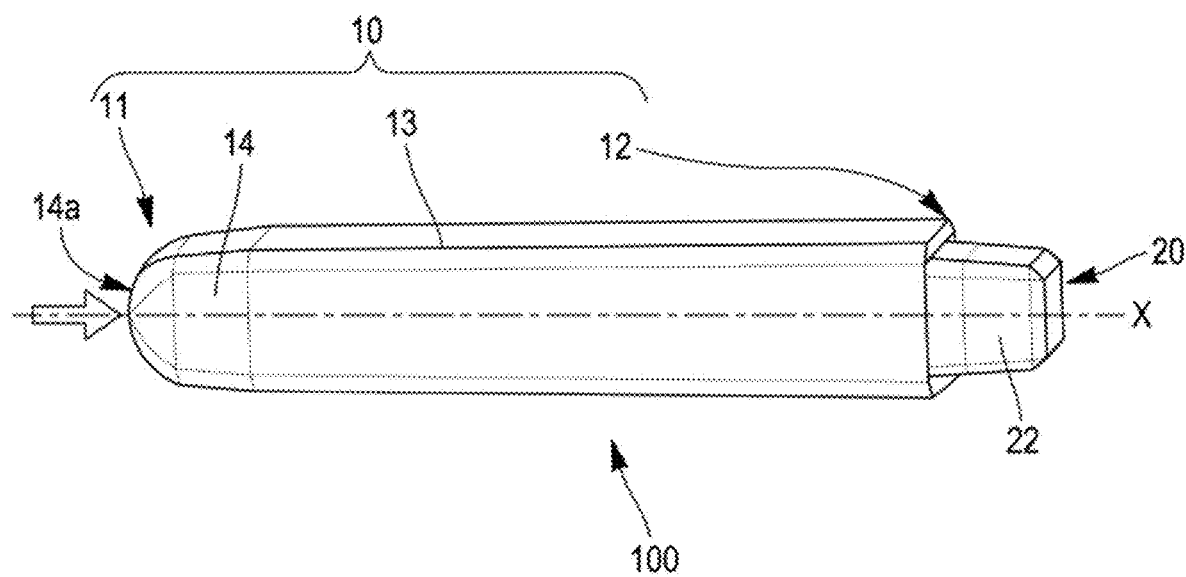
FIGS. 3A and 3B, respectively, show a perspective view and a sectional view of a double packaging according to the present disclosure, when pressure is applied to the membrane of the outer container, to extract the inner container hosting the object.
Figure 3B:
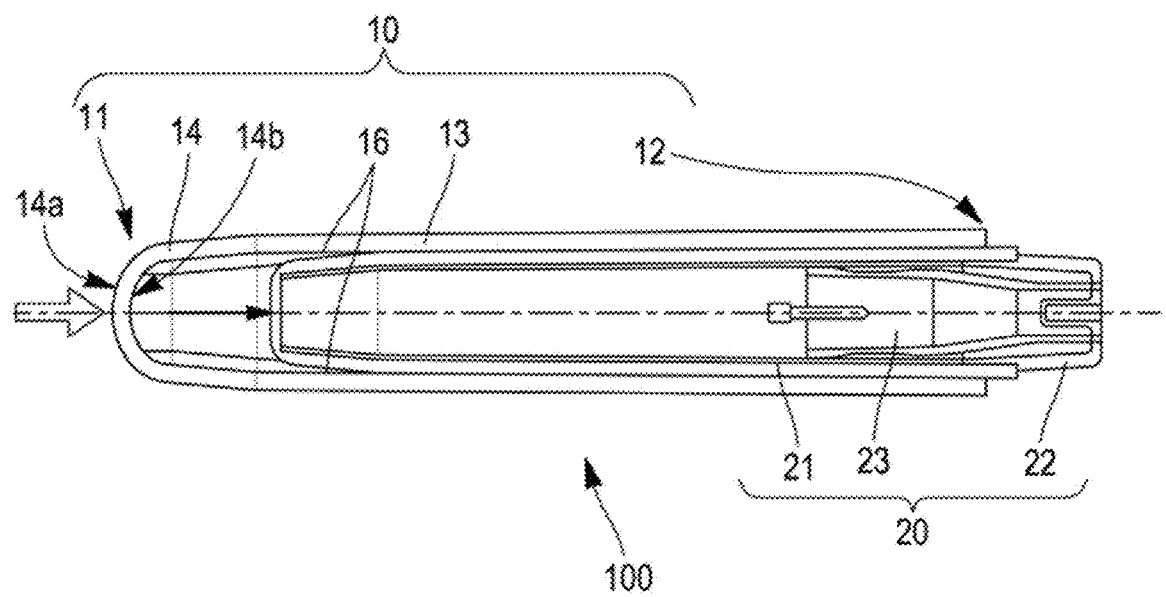

According to an advantageous embodiment, the object holder 23 is formed from a flexible and deformable material, such as, for example, a thermoplastic elastomer (TPE), polystyrene-b-polyethylene-butylene-b-polystyrene (SEBS), or silicone. The object holder 23 has a generally tubular shape, defining a housing having an oval cross-section shape in which the object is held. One end of the object holder 23 is held integral with the cap 22. The other end of the object holder 23 is open and allows access to the object 1. The object 1 may protrude from the open end of the object holder 23 (as illustrated in FIGS. 2*b* and 3*b*) or alternatively be completely included in the housing formed by the object holder 23. The material, the thickness and the dimensions of the object holder 23 are chosen so that the internal walls of the object holder 23 are pressed against the object 1 and prevent it, by friction, from being extracted from this housing by gravity or when the double packaging 100 is shaken. By way of example, the oval section of the housing defined by the object holder 23 may have a diameter less than or equal to a dimension of the object 1, the latter thus being held pressed against the internal walls of the object holder 23.

According to another embodiment, the object holder 23 is formed from a rigid material, for example plastic, such as acrylonitrile butadiene styrene (ABS), polycarbonate (PC), ABS-PC, a mixture of the above-mentioned compounds, polyesters or co-polyesters, or polypropylene (PP). The object holder 23 has a generally tubular shape, defining a housing in which the object 1 is held. One end of the object holder 23 is held integral with the cap 22. The other end of the object holder 23 is open and allows the object 1 to be maintained, for example by screwing; object 1 can be accessed by unscrewing it from this end.

Returning to the description of the membrane 14, as stated above, the membrane 14 has an outer face 14*a* and an inner face 14*b*. The membrane 14 is further configured so that pressure (shown diagrammatically by the white arrow, in FIGS. 3*a* and 3*b*) applied to its outer face 14*a*, along the longitudinal axis X, pushes its inner face 14*b* against the internal container 20, and in particular against the end of the body 21. This thrust (shown diagrammatically by the black arrow in FIG. 3B) is possible due to the deformation (not shown) of the membrane 14 in a direction going towards the inside of the external container 10. In the absence of the closure system, the thrust causes the internal container 20 to exit, at the second end 12 of the external container 10.

When the object 1 is to be used, the double packaging 100 is introduced into the sterile room by a first operator, who grasps the external surface of the external container 10, of which the surface is contaminated due to the station in the storage zone for the double packaging 100. In a sterile room, the first operator removes the closure system (for example, removal of a sealed cover), thus opening the second end 12 of the external container 10. The first operator then applies pressure to the outer face 14*a* of the membrane 14, along the longitudinal axis X: the inner face 14*b* of the membrane 14 then comes into contact with the end of the body 21 of the internal container 20 and pushes this out of the external container 10, via its open end 12 (FIGS. 3*a* and 3*b*). A second operator (sterile) can then grasp the internal container 20, which is completely sterile, at the level of the cap 22 which protrudes from the second end 12 of the external container 10.

The double packaging 100 according to the present disclosure prevents the second operator from being in contact with the contaminated external surface of the external container 10. It also facilitates the provision of the internal container 20, by the first operator (non-sterile) to the second operator (sterile), without shock or risk of accidental fall and contamination. The internal container 20 is only handled by the second operator, in sterile condition, who can then open the cap 22 and extract the object 1 from the object holder 23. The extraction of the object 1 from the object holder 23 is carried out by simple pressure on the side walls of the object holder 23, when the latter is formed from flexible and deformable material as mentioned previously in an advantageous embodiment. In fact, pressure on the object holder 23 is capable of deforming and widening the object holder 23, thereby releasing the object 1.

Advantageously, the walls 13 of the external container 10 comprise at least a first rib 16 on an interior surface (FIGS. 2*b* and 3*b*). The (at least one) first rib 16 is preferably positioned on the side of or near the first end 11 of the external container 10. This first rib 16 is adapted to keep the internal container 20 wedged in the external container 10, due to mechanical friction between the first rib(s) 16 and the wall of the internal container 20, when no pressure is applied to the membrane 14. The (at least one) first rib 16 may extend parallel to the longitudinal axis X or along an axis forming a non-zero angle with the longitudinal axis X. Preferably, several first ribs are uniformly distributed over the interior surface of the walls 13.

Due to the presence of this (or these) first rib(s), it is essential to apply pressure on the membrane 14 to push the internal container 20 and loosen it in order to bring it out at the level of the second end 12 of the external container 10. This avoids the risks of the internal container 20 unexpectedly leaving the external container 10, when the closure system has been removed and when the second open end 12 of the external container 10 is inadvertently oriented downwards.

The membrane 14 can have different shapes. Advantageously, as illustrated in the accompanying figures, the outer face 14*a* of the membrane 14 has a convex shape, in its "rest" state, that is to say when no pressure is applied to the membrane 14. The membrane 14 can have a general hemispherical or semi-ellipsoid shape. Preferably, when the internal container 20 is completely disposed in the external container 10 and the membrane 14 is in its rest state, the end of the body 21 is in contact with all or part of the inner face 14*b* of the membrane 14, as illustrated in FIG. 2B.

Note that the inner face 14*b* of the membrane 14 may include at least a second rib, adapted to keep the internal container 20 wedged in the external container 10, by friction between the second rib and the wall of the internal container 20, when no pressure is applied to the membrane 14 (that is to say in its resting state). The (at least one) second rib may be implemented with or without the (at least one) first rib 16.

The membrane 14 of the external container 10 can be formed from a material chosen from thermoplastic elastomers (TPE), polystyrene-b-polyethylene-butylene-b-polystyrene (SEBS) and silicone.

The walls 13 of the external container 10 and the body 21 of the inner container 20 can be formed from a rigid plastic material, such as acrylonitrile butadiene styrene (ABS), polycarbonate (PC), ABS-PC, a mixture of the compounds mentioned above, polyesters or co-polyesters, or polypropylene (PP).

The cap 22 of the internal container 20 can be formed from a flexible material chosen from thermoplastic elastomers (TPE), polystyrene-b-polyethylene-butylene-b-polystyrene (SEBS) and silicone, or from a rigid material such as acrylonitrile butadiene styrene (ABS), polycarbonate (PC), ABS-PC a mixture of the above-mentioned compounds, polyesters or co-polyesters, or polypropylene (PP). Note that if the cap 22 and the object holder 23 are formed from the same material, they can be formed in one piece rather than in two assembled pieces.

The membrane 14 is advantageously fixed to the walls 13 of the external container 10 by overmolding or by bi-injection, techniques well known for the manufacture of parts made of plastic material(s).

Of course, the invention is not limited to the embodiments and examples described, and it is possible to make variant embodiments without departing from the scope of the invention as defined by the claims.

What is claimed is:

1. A double packaging structure for an object, comprising:
   a hollow external container extending generally along a longitudinal axis and comprising a closed first end, an open second end and walls connecting the first and the second end, the second end configured to be closed by a closure system; and
   an internal container disposed inside the external container, the internal container including a hollow body and a cap, the hollow body configured to receive the object therein; and
   wherein the external container comprises a membrane closing the closed first end of the hollow external container, the membrane configured to deform responsive to application of pressure to the membrane, the membrane having an outer face and an inner face and configured such that pressure applied to the outer face of the membrane along the longitudinal axis pushes the inner face of the membrane against the internal container and causes the internal container to exit the external container at the second end of the external container, in the absence of the closure system; and
   wherein the cap of the internal container is configured to accommodate an object holder intended to fix the object securely inside the body.

2. The double packaging structure of claim 1, wherein the walls of the external container define a tubular shape having a central axis defining the longitudinal axis and having a square, rectangular, polygonal, circular or elliptical cross-sectional shape.

3. The double packaging structure of claim 2, wherein the walls of the external container comprise at least a first rib on an interior surface thereof, the first rib being adapted to maintain the internal container wedged in the external container when no pressure is applied to the membrane.

4. The double packaging structure of claim 3, wherein the at least a first rib is near the first end of the external container.

5. The double packaging structure of claim 4, wherein the membrane is configured to elastically deform in response to application of pressure to the membrane.

6. The double packaging structure of claim 5, wherein the outer face of the membrane has a convex shape when no pressure is applied to the membrane.

7. The double packaging structure of claim 1, wherein the membrane has a generally hemispherical or semi-elliptical shape.

8. The double packaging structure of claim 6, wherein the inner face of the membrane comprises at least a second rib, the at least a second rib adapted to hold the internal container wedged in the external container when no pressure is applied to the membrane.

9. The double packaging structure of claim 6, wherein the cap of the internal container includes object holder.

10. The double packaging structure of claim 9, wherein the object holder is formed from a flexible or rigid plastic material and has a generally tubular shape defining a housing in which the object is held.

11. The double packaging structure of claim 1, wherein the walls of the external container and the body of the internal container are formed from at least one rigid plastic material chosen from among acrylonitrile butadiene styrene (ABS), polycarbonate (PC), a mixture of acrylonitrile butadiene styrene and polycarbonate (ABS-PC), polyesters or co-polyesters, or polypropylene (PP).

12. The double packaging structure of claim 1, wherein the cap of the internal container is formed from at least one flexible plastic material chosen from among thermoplastic elastomers (TPE), polystyrene-b-polyethylene-butylene-b-polystyrene (SEBS) and silicone, or from a rigid plastic material such as acrylonitrile butadiene styrene (ABS), polycarbonate (PC), a mixture of acrylonitrile butadiene styrene and polycarbonate (ABS-PC), polyesters or co-polyesters, or polypropylene (PP).

13. The double packaging structure of claim 1, wherein the membrane of the external container is formed from a material chosen from among thermoplastic elastomers (TPE), polystyrene-b-polyethylene-butylene-b-polystyrene (SEBS) and silicone.

14. The double packaging structure of claim 1, wherein the membrane is fixed to the walls of the external container by overmolding or by bi-injection.

15. The double packaging structure of claim 1, further comprising the closure system, the closure system being formed by a cover fixed on the walls of the external container at the second end, by sealing, thermo-welding, or bonding.

16. The double packaging structure of claim 1, wherein the walls of the external container comprise at least a first rib on an interior surface thereof, the first rib being adapted to maintain the internal container wedged in the external container when no pressure is applied to the membrane.

17. The double packaging structure of claim 1, wherein the membrane is configured to elastically deform in response to application of pressure to the membrane.

18. The double packaging structure of claim 1, wherein the outer face of the membrane has a convex shape when no pressure is applied to the membrane.

19. The double packaging structure of claim 1, wherein the cap of the internal container includes the object holder.

* * * * *

UNITED STATES PATENT AND TRADEMARK OFFICE
CERTIFICATE OF CORRECTION

| | |
|---|---|
| PATENT NO. | : 11,583,359 B2 |
| APPLICATION NO. | : 16/919796 |
| DATED | : February 21, 2023 |
| INVENTOR(S) | : Maxime Clavel |

It is certified that error appears in the above-identified patent and that said Letters Patent is hereby corrected as shown below:

In the Claims

Claim 9, Column 8, Line 5, change "includes object" to --includes the object--

Signed and Sealed this
Twenty-ninth Day of August, 2023

*Katherine Kelly Vidal*

Katherine Kelly Vidal
*Director of the United States Patent and Trademark Office*